United States Patent [19]

Archer

[11] Patent Number: 4,580,520

[45] Date of Patent: Apr. 8, 1986

[54] FATIGUE INDICATOR

[75] Inventor: Michel Archer, La Celle Saint Cloud, France

[73] Assignee: Societe Technique d'Accessoires Specialises S.T.A.S., Satrouville, France

[21] Appl. No.: 667,262

[22] Filed: Nov. 1, 1984

[30] Foreign Application Priority Data

Nov. 4, 1983 [FR] France ............... 83 18059

[51] Int. Cl.⁴ ............................. G01N 19/08
[52] U.S. Cl. ............................ 116/212; 73/762; 73/787
[58] Field of Search ............. 116/212; 73/760, 762, 73/774, 775, 787, 799, 810, 831, 856

[56] References Cited

U.S. PATENT DOCUMENTS 3,572,091 3/1971 McFarland ............... 73/760
4,409,841 10/1983 Archer ..................... 116/212
4,502,337 3/1985 Archer ..................... 73/762

Primary Examiner—Charles Frankfort
Assistant Examiner—Patrick R. Scanlon
Attorney, Agent, or Firm—Karl F. Ross; Herbert Dubno

[57] ABSTRACT

The invention relates to a fatigue indicator for mechanical parts subjected to repeated stresses, which comprises two thick elements spaced apart from one another and joined together by a thin web having a slit, these two elements being incorporated in the part or fixed thereto so as to move with respect to one another upon application of stress on the mechanical part in a plane which is parallel to the plane of the web, the thin web being thus subjected to a shearing stress in its plane, and wherein the slit of the thin web extends from one of the edges of the web in the direction of relative movement to a blind end so that, when the part is stressed, two cracks appear from corners of the blind end of the slit, extend progressively in the web and finish by reaching the opposite edge of the web or joining cracks coming from this opposite edge, the web thus being detached or practically detached.

4 Claims, 3 Drawing Figures

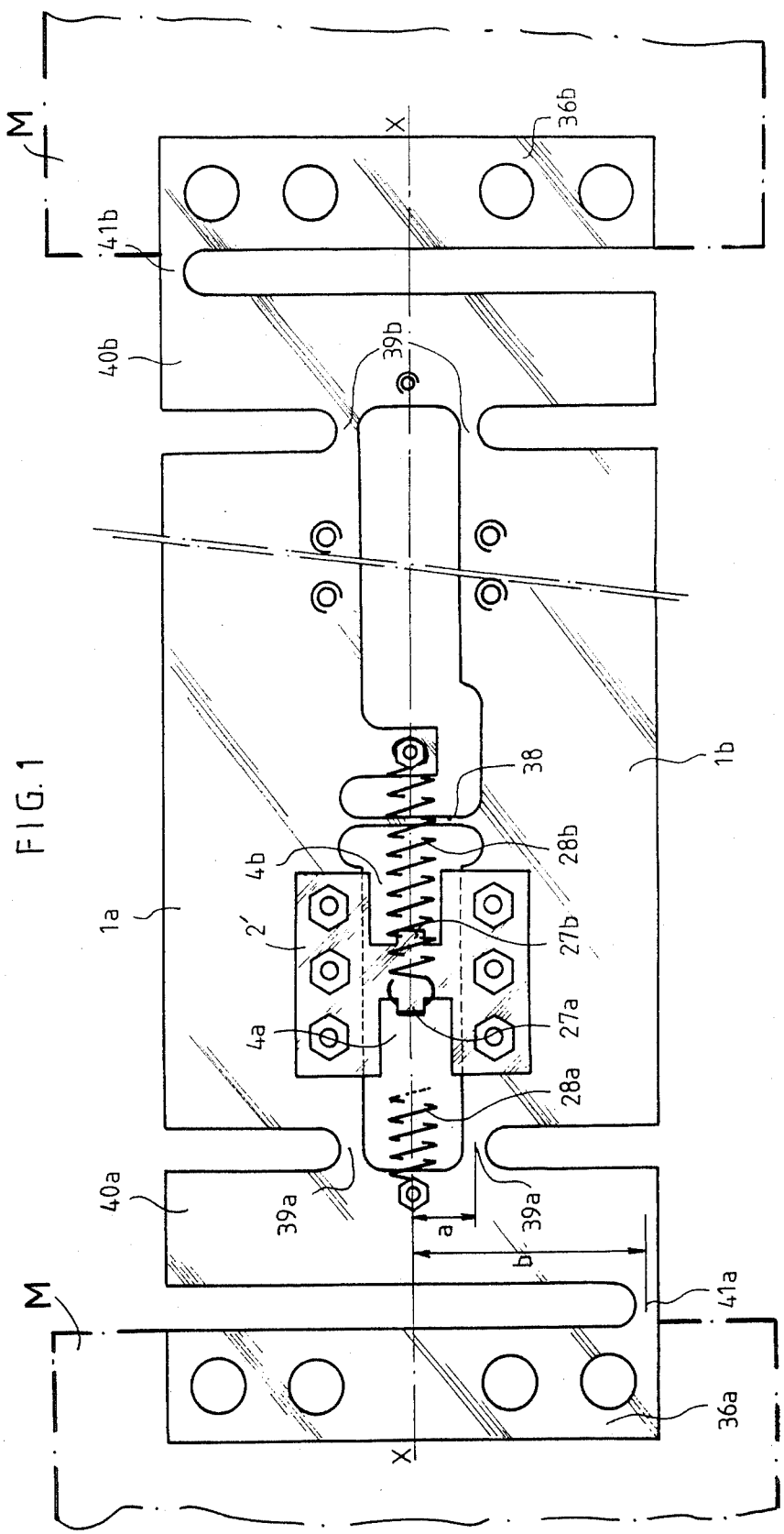

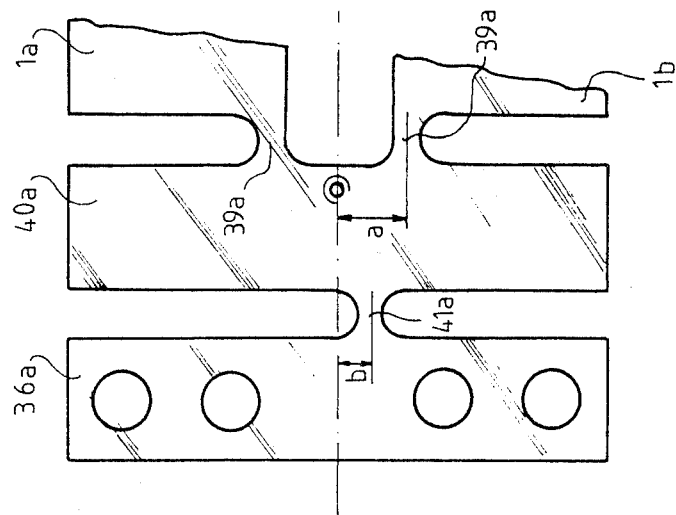
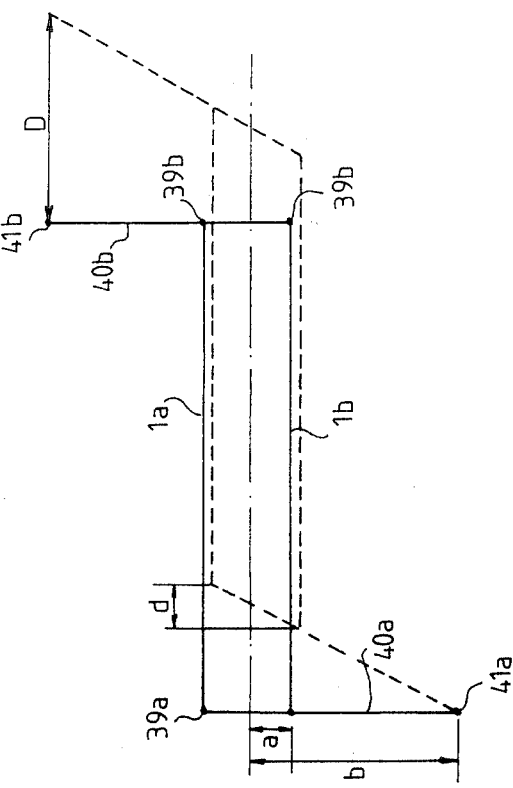

FATIGUE INDICATOR

FIELD OF THE INVENTION

The present invention relates to a fatigue indicator for mechanical parts subjected to repeated stresses, which comprises two thick elements spaced apart from one another and joined together by a thin web having a slit, these two elements being incorporated in the part or fixed thereto so as to move with respect to one another in a plane which is parallel to the plane of the web.

BACKGROUND OF THE INVENTION

In my U.S. Pat. No. 4,409,841, I described a fatigue indicator of this kind in which the thick elements are disposed so as to be spaced apart from each other in a direction substantially perpendicular to their direction of relative movement when the part is stressed, the thin web thus being subjected to a shearing stress in its plane, and in that the slit in the thin web extends from one of the edges of the web in the direction of relative movement so that, when the piece is working, two cracks appear from the ends of the bottom of the slit, extending progressively in the web and finish by reaching the opposite edge of the web or joining cracks coming from this opposite edge, the central zone of the web thus being detached, or pratically detached.

This fatigue indicator is intended essentially for indicating the fatigue of a part subjected to traction or compression stresses.

When the thick elements of the fatigue indicator are fixed directly to the part to be monitored, the relative movements of these two thick elements is equal to the relative movement of the two positions on the part to which they are fixed. This latter movement is a characteristic which depends on the mechanical part and whose value cannot be modified. Now it may happen, in particular in the case of light alloy parts, that this value is incompatible with the characteristics of the fatigue indicator.

OBJECT OF THE INVENTION

The object of the present invention is to provide an improvement in a fatigue indicator of the above kind for overcoming the above described difficulty.

SUMMARY OF THE INVENTION

According to the present invention, the thick elements are joined at each of their ends by a flexible zone to an intermediate portion which is itself connected by a flexible zone to another portion for direct fixing to the mechanical part or member to be monitored. When the two portions secured to the member move with respect to each other, the intermediate portions between the flexible zones form levers and the value of the relative movement of the thick elements is equal to the value of the movement of the securing portions multiplied by a coefficient depending on the distances from the flexible zones to the longitudinal axis of the fatigue indicator. By suitably choosing the location of these flexible zones, the value of the movement of the thick elements may be reduced at will or on the contrary increased.

BRIEF DESCRIPTION OF THE DRAWING

There is described hereafter by way of a non limitative example one embodiment of the fatigue indicator according to the present invention with reference to the accompanying drawings in which:

FIG. 1 is an elevational view of the device according to the invention;

FIG. 2 is a diagrammatic view of this embodiment showing the movement of the different parts of the fatigue indicator and FIG. 3 is a detail of another embodiment of the invention.

SPECIFIC DESCRIPTION

In FIG. 1, the indicator comprises two thick parts 1a and 1b spaced apart from each other and joined together by several thin webs 2' only one of which is shown; each of these webs has two slits or slots 4a and 4b parallel to the longitudinal direction of parts 1a and 1b, the end of each of these slits comprising a lug 27a or 27b which projects outside the plane of the web, one on one side of this plane and the other on the opposite side; these lugs serve for securing springs 28a and 28b. The parts 1a and 1b are further joined together by flexible bridges 38 disposed between two adjacent thin webs.

At each of their ends, parts 1a and 1b are joined by flexible zones 39a and 39b to the intermediate portions 40a and 40b which are in turn joined by flexible zones 41a and 41b to portions 36a and 36b serving for securing the fatigue indicator to the part M to be monitored.

The two flexible zones 39a and 39b are disposed substantially symmetrically with respect to the median longitudinal axis X—X of the fatigue indicator and are each spaced apart from this axis by a distance a.

The flexible zones 41a and 41b are disposed one on one side of the axis X—X and the other on the opposite side. Each of them is spaced transversely from axis X—X by a distance b which is here greater than a.

It can be seen from FIG. 2 that, when the two securing parts 37a and 36b, i.e. the positions on the structure to be monitored to which these parts are fixed, move away from each other or toward each other by a distance d, the two thick parts 1a and 1b move with respect to each other by a distance d smaller than D. It can readily be seen that we have:

$$d = D(a/b).$$

In the arrangement of FIG. 3, the flexible zones 41a and 41b are spaced from axis X—X by a distance b smaller than a. In this case, when the two securing parts 36a and 36b move longitudinally with respect to each other over a distance D, the two thick parts 1a and 1b move with respect to each other by a distance d greater than D.

It can be seen that by suitably choosing the ratio a/b, suitable values may be obtained for the movement of the thick parts 1a and 1b, whatever the distances over which the securing parts 36a and 36b, and so the positions on the structure to be monitored where these parts are fixed, move.

What I claim is:

1. In a fatigue indicator for a mechanical member subjected to repetitive stress, comprising an elongated flat body formed with a pair of elongated thick elements spaced apart from one another across a longitudinal axis of said body and connected to each other by at least one thin web formed with a slot and having a pair of free opposite edges, the pair of thick elements being so joined with the mechanical member that said elements are displaceable relative to one another in a plane parallel to the plane of the web by stress applied to said member, the web being subjected to shear force in its plane by the relative displacement of said elements, the slot of said web extending parallel to said axis from one of the edges of said web and terminating short of the opposite edge in a blind end having two corners whereby with application of said stress to the member, two cracks develop at said corners of the end of said slot and are propagated progressively in the web towards an opposite edge thereof so that said cracks meet other cracks propagating generally in a direction away from said opposite edge to substantially sever said web, the improvement wherein said pair of thick elements are joined at each of their respective ends to respective intermediate portions by a first flexible zone offset from said axis, each respective intermediate portion being joined to said mechanical member to be montiored by a second flexible zone offset from said axis.

2. The improvement defined in claim 1, wherein each of said second flexible zones is disposed on an opposite side of said axis.

3. The improvement defined in claim 2, wherein said second flexible zones are offset from said axis by a distance greater than the offset of said first flexible zones.

4. The improvement defined in claim 2, wherein said second flexible zones are offset from said axis by a distance less than the offset of said first flexible zones.

* * * * *